US007417174B2

(12) United States Patent
Hicks, Jr. et al.

(10) Patent No.: US 7,417,174 B2
(45) Date of Patent: Aug. 26, 2008

(54) RESORBABLE LAMINATED REPAIR FILM AND METHOD OF USING SAME

(75) Inventors: Wesley L. Hicks, Jr., Angola, NY (US); Rena Bizios, Troy, NY (US); Frank V. Bright, Williamsville, NY (US); Joseph A. Gardella, Buffalo, NY (US); Robert Hard, Buffalo, NY (US); Jamson S. Lwebuga-Mukasa, Getzville, NY (US); Alexander N. Cartwright, Williamsville, NY (US); Bahattin Koc, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 733 days.

(21) Appl. No.: 10/986,547

(22) Filed: Nov. 11, 2004

(65) Prior Publication Data

US 2005/0131328 A1 Jun. 16, 2005

Related U.S. Application Data

(60) Provisional application No. 60/519,013, filed on Nov. 11, 2003.

(51) Int. Cl.
*A61F 13/00* (2006.01)
(52) U.S. Cl. .......................................... 602/41; 602/48
(58) Field of Classification Search ............. 602/41–59
See application file for complete search history.

(56) References Cited

U.S. PATENT DOCUMENTS

| 5,741,566 | A | * | 4/1998 | Hogstrom et al. | 428/35.2 |
| 5,983,604 | A | * | 11/1999 | Wilfong et al. | 53/449 |
| 6,544,660 | B1 | * | 4/2003 | Lind et al. | 428/516 |
| 6,632,383 | B1 | * | 10/2003 | Peet | 264/46.1 |

* cited by examiner

*Primary Examiner*—Michael A. Brown
(74) *Attorney, Agent, or Firm*—Hodgson Russ LLP

(57) ABSTRACT

The present invention provides a reepithelialization/wound healing implant device comprising a barrier layer and one or more polymer layers doped with agents that promote one or more processes in reepithelialization/wound healing. The implant: [a] provides a temporary mechanical/chemical barrier to species within the external environment that inhibit epithelial migration (e.g., unbalanced production/expression of granulation tissue, inhibitory proteins); [b] biodegrades at an appropriate rate while tissue remodeling is occurring; and [c] delivers active cytokines and growth factors in a choreographed pattern to promote reepithelialization.

25 Claims, 8 Drawing Sheets

RESORBABLE LAMINATED REPAIR FILM AND METHOD OF USING SAME

This application claims priority to U.S. provisional application No. 60/519,013, filed on Nov. 11, 2003, the disclosure of which is incorporated herein by reference.

This work was funded by Grant No. CHE-0078101 from the National Science Foundation. The Government has certain rights in the invention.

FIELD OF THE INVENTION

The present invention relates generally to the field of wound healing and more particularly provides a synthetic laminated repair film which promotes reepithelialization.

DISCUSSION OF RELATED ART

There are over 40 million surgical procedures preformed across the United States each year (National Center for Health Statistics; Center of Disease Control 2000). The positive outcome of these operations is as dependent on successful wound repair as it is the physicians' clinical skills.

Wound repair consists of three overlapping phases, described linearly for the purpose of clarity as inflammation, proliferation and wound maturation (Witte and Barbul 1997). Different types of wounds undergo each phase of wound healing to varying degrees, but the phases themselves remain consistent regardless of the tissue injured. By definition acute wounds go through all three phases of wound repair with the restoration of normal physiologic function. Chronic or non-healing wounds never complete the phases of the repair process and do not reestablish a functional physiologic result.

Reepithelialization is part of the proliferative phase of wound repair and in addition to being a biologic end result of healing, is an active and essential contributor to the repair process itself Epithelial migration and proliferation after injury are vital to the reestablishment of normal architecture and function in virtually every organ system.[1-6] In addition recent published results support the view that the presence of epithelium and the act of reepithelialization improve overall wound healing. It is believed that it is the bi-directional exchange of repair mediators, (i.e. growth factors/cytokines), between epithelial and connective tissue elements that enhance the successful coordination of wound repair.

The epithelial basement membrane is an active physiologic structure where biologic cues (e.g. growth factor/cytokines) between epithelium and connective tissue are exchanged. In addition to serving as structural support for the overlying epithelium, the basement membrane acts as a selective barrier and storage compartment for proteins secreted by the epithelium and connective tissue cells.

Some examples of wound healing relevant to the clinical setting include: (1) endothelial migration and hyperplasia demonstrated in the vascular tree after graft placement, (2) debilitating chronic injury and repair cascade of Crohn's disease and Ulcerative Colitis (gastrointestinal tract), (3) visual impairment resulting from corneal injury, (4) skin re-growth following burn injuries, and (5) mucositis (secondary to chemotherapeutic treatment).

SUMMARY OF THE INVENTION

The present invention provides a resorbable, laminated repair film ("RLRF" hereafter) which is placed into contact with an area of the tissue injury to facilitate reepithlialization/would healing. The RLRF selectively increases and sustains the rate of reepithelialization (migration/proliferation) of epithelium after injury and improves general wound repair. The RLRF comprises at least two layers. A first layer serves as a barrier layer. In operation, the barrier layer provides a temporary obstruction to unregulated in-growth of tissue and/or sub-epithelial release of factors that impede reepithelialization. The layer is characterized by a biodegradability upon hydrolysis of the polymers as well as the ability to physically block inhibitory factors from reaching and interfering with reepithelialization at the wound site. Generally, it is believed that these inhibitory factors are generated in or around the wound site. The barrier layer preferably breaks down at a rate that optimizes and augments the rate of reepithelialization based on the tissue/organ site being treated (see FIG. 1). The degree and rate of degradability are chosen accordingly.

The barrier layer has an external side that, in operation, apposes the wound site. On the other side (the lumenal side) of the barrier layer are disposed one or more biodegradable polymer layers comprising reepithelialization/wound healing agents such as proteins, cell nutrients, etc. These agents, hereafter called "repair mediators," are released in a choreographed fashion. By "choreographed," it is meant the concentration, rate, duration and/or the sequence of release of the repair mediators can be dictated. For example, the arrangement and thickness of the layers in the RLRF, protein loading and characteristics of the polymers and repair mediators can affect the release of the repair mediators. Abbreviations used are as follows: PLA for poly(1-lactic acid); PGA for poly(glycolic acid); PLLA for poly(L-lactic acid); PLGA for poly(dl-lactic-co-glycolic acid); PDMS for poly(dimethylsiloxane); PEO for poly(ethylene oxide); PLLD for poly(L-lysine dendrimer); and AOT for sodium diisooctylsulfoccinate.

DETAILED DESCRIPTION OF THE INVENTION

Figure 1A:
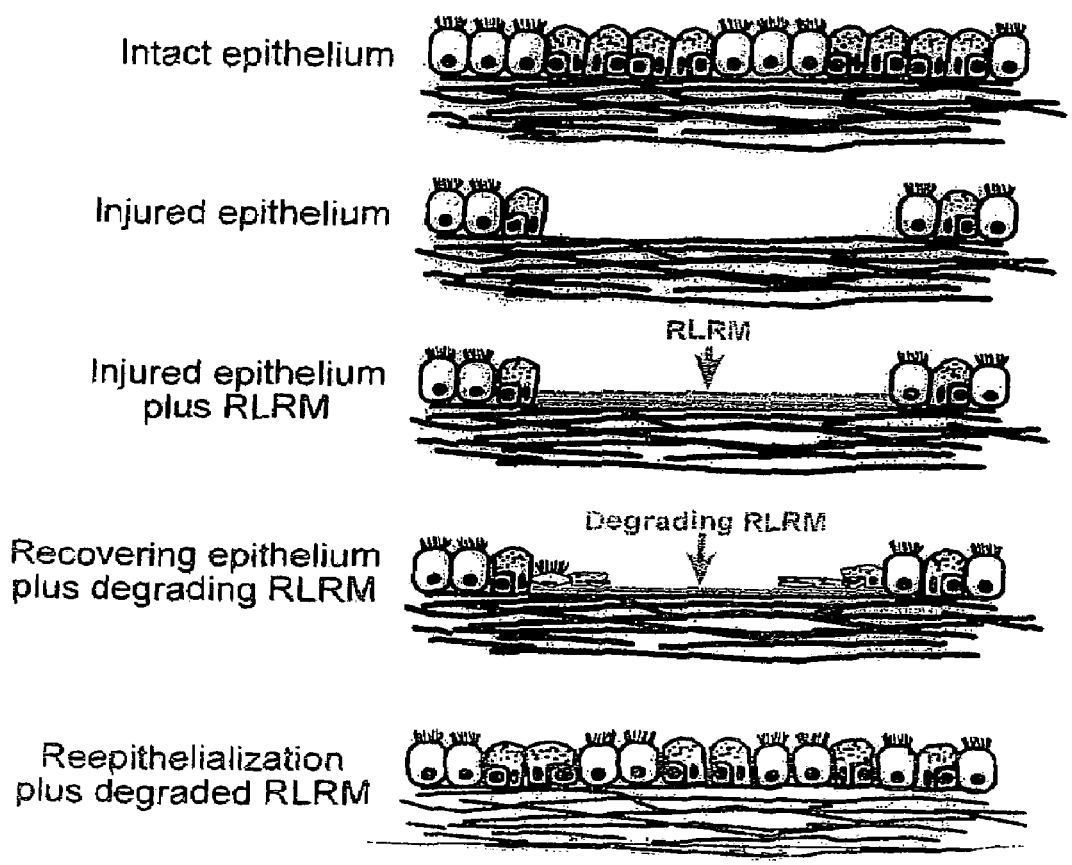
FIG. 1A is a schematic representation of the wound healing process using resorbable laminated repair film (RLRF).
Figure 1B:
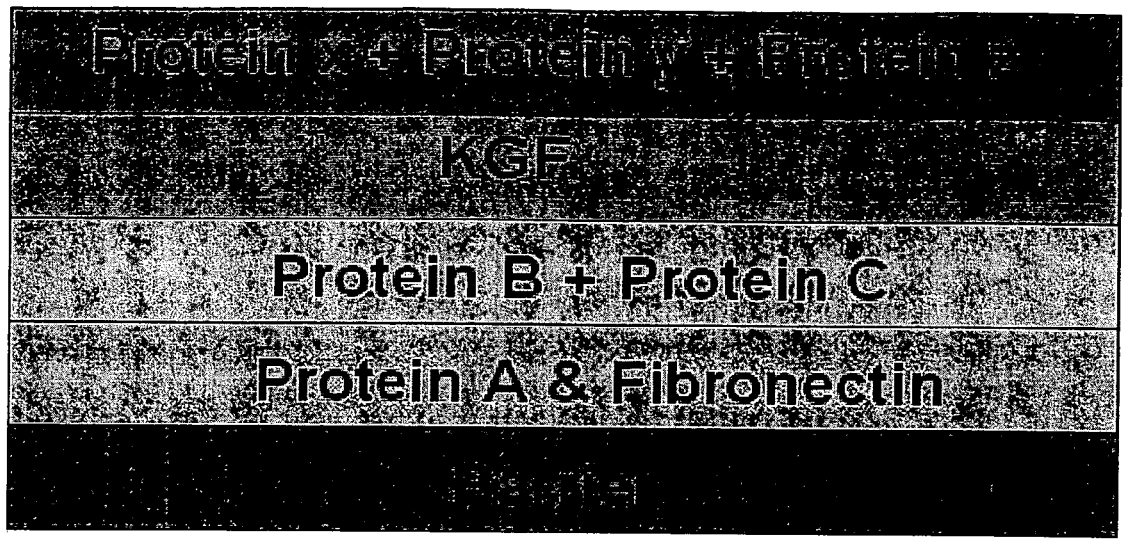
FIG. 1B is a schematic representation of the RLRF.

The RLRF of the present invention comprises a multilayered structure including a barrier layer and one or more repair mediator doped layers (FIG. 1B). The term "repair mediators" as used herein means a factor that enables, enhances or sustains the rate of reepithelialization (migration/proliferation) after tissue injury. The repair mediators may be proteins, polypeptides, peptides or other cell nutrients (i.e., glucose) which can improve the inherent rate of epithelial migration/proliferation during wound repair.

The RLRF comprises a laminated multilayer construct as shown in FIG. 1, wherein each layer is comprised of one or more biodegradable polymers. The barrier layer exhibits a degradation rate and barrier properties that can be tailored to a desired application. Additional layers can be effectively installed to promote reepithelialization and/or wound healing.

The repair mediator-doped layers comprise biodegradable polymer formulations into which are doped repair mediators (such as, for example, KGF, transforming growth factor (TGF)-α, interleukin-1 (IL-1), epidermal growth factor (EGF)) and other agents that promote reepithelialization. The various layers and functions of the present device are discussed in more detail below.

While not intending to be bound by theory, it is thought that the RLRF promotes wound healing by one or more of the following processes; 1) Providing a temporary chemical and physical barrier to agents that are inhibitory to epithelial migration/proliferation. 2) Delivering agents which promote healing, such as active proteins (e.g., cytokines and growth factors) and cell nutrients (e.g., glucose), in a choreographed fashion so as to promote rapid epithelial repair (migration and proliferation), 3) Providing an appropriate resorbable provisional extracellular matrix onto which epithelial cells can migrate and proliferate. Thus, the membrane device blocks unregulated in-growth of tissue while promoting reepithelialization.

The barrier layer is biodegradable. It has an external surface that is placed apposing the wound area, and a lumenal surface which apposes a protein-doped layer. The barrier layer blocks transport of species that inhibit reepithelialization on the RLRF. Furthermore, the barrier layer has a desired degree of permeability to water, which can be controlled by choice of polymers as further described below.

In one embodiment, the lumenal surface of the barrier layer yields a surface chemistry that is conducive to overlayer formation. For example, this can be achieved by the use of interfacial chemistries that promote interchain mixing but limit the mixing to a very thin, but strongly mixed layer. In a non-limiting example, if the overlayer contains PLA, then a barrier layer which has PLA at the interfacial surface can promote adhesion between the layers.

Materials that can be used in the formation of the barrier layer are polymeric materials which undergo hydrolytic degradation. Preferred are polymers that form layers in which the external surface, the lumenal surface or both have enhanced impenetrability with respect to water. For example, a siloxane-containing polymer (for example, 2-10% siloxane in an ABA poly(dimethylsiloxane) (PDMS) polyester block copolymer) can result in siloxane segment segregation at the surface of the layer FIG. 1C). In some instances the surface of such a film can be 100% siloxane even though the bulk copolymer contains significantly less siloxane. This feature provides a barrier layer architecture because siloxanes serve to block water penetration and the subsequent diffusion of other species through the membrane.

The polymers in the barrier layers can be comprised of homopolymers (e.g., PLA, PGA), polymer blends (e.g., PGA+PLLA), copolymers (e.g., PLGA), fluorocarbon capped polymers (e.g., PLA-Fluorocarbon), and block copolymers (e.g., PLA-PDMS-PLA and PLA-PEO-PLA), block copolymers of PEO and PLA components. In addition, the polymers may also be poly anhydrides such as polysebacic anhydride (PSA) and polyfumaric anhydride (PFA), and polyamino acids such as polyaspartic acid.

Some further examples of polymers useful for preparing the barrier layer include copolymers based on combining hydrolytically degradable polyesters and fluorocarbon surface chemistry. Like siloxanes, fluorocarbon chemistry can be used to inhibit barrier layer penetration by water. A series of copolymers where the terminal fluorocarbon chains of two lengths $[CF_3(CF_2)_m(CH_2)_n]$, where F7C1 and F10C2 represent m=6 and n=1 and m=9 and n=2, respectively] are covalently bound as end groups to L- and DL-polylactides (PLA) and poly(lactide-co-glycolide) (Chen et al, 1998, Applied Spectroscopy, 52:361-366) have been synthesized. By using ring-opening polymerization and the fluorocarbon substitution at terminal —OH groups, new polyesters with 1, 2, and 4 fluorocarbon end groups were obtained (F-polyesters). Angle-dependent X-ray photoelectron spectroscopy (XPS or ESCA) revealed that the fluorocarbon end groups segregated to the surface. Additionally, the surface coverage of fluorocarbon groups increased with concentration and length of fluorocarbon end groups. The F-polyester's surface composition can also be controlled by blending these polymers with polyesters or by changing the fluorocarbon architecture. The ESCA data of F-polyesters after in-vitro hydrolysis at a pH of 11.4 and results from the F-polyester with a longer fluorocarbon end group (F10C2-) showed that the surface erosion occurs at the topmost surface region during the initial hydrolysis period. The F-polyester having a short fluorocarbon group (F7C1-) showed a progressive decrease of surface fluorocarbon concentration as a function of hydrolysis time. This result may be explained by a decrease in water permeation into the sample bulk of F10C2-L-PLA that arises from the greater segregation of fluorocarbon groups at the topmost polymer surface.

Another example of copolymers are those that are prepared incorporating PDMS segments at very low (ca., 0.7-3% by weight) compositions. The ESCA data for these polyester-b-PDMS-b-polyester triblock copolymers (not shown) demonstrated that the film surface is enriched in PDMS (greater than 80% of the surface area) when compared to the bulk polymer composition. Like siloxanes and fluorocarbon groups, the segregated PMDS component can serve to inhibit water penetration of the barrier layer.

The barrier layer is designed to block the deleterious species/agents for a desired amount of time (which can be selected) and to then resorb (biodegrade). Biodegradation and membrane breakdown are enhanced by the ability of the barrier layer to absorb water. Thus, for example, the addition of siloxane groups to polymers to create siloxane polymers as described above generally results in a polymer which forms a layer with increased water resistance and break down time. In general, some parameters which can be varied in order to produce a layer with the desired breakdown time are layer thickness, density, and porosity, as well as the pH of the local microenvironment. Thickness is dictated by preparation parameters. Increased density can generally be achieved by the use of polymers with a longer chain-length. The porosity of the polymer can be varied through polymer processing approaches, such as solvent volatility, temperature changes during solvent evaporation, addition of volatile gases during film preparation, templating/extraction, etc. For a given polymer, greater porosity generally gives more rapid hydrolysis and a correspondingly increased rate of repair mediator release. The pH of the local microenvironment (intestine, esophagus, eye, etc.) also has an effect on the hydrolysis of the polymer and rate of release of repair mediator. In general, depending upon the particular polymer, acidic or basic conditions may catalyze or inhibit polymer hydrolysis.

The polymers useful in the present invention can contain other ingredients, such as additives (such as surfactants and the like), as long as the ingredients do not completely prevent release of the repair mediator or adhesion of overlayers.

The repair mediator-doped layers are also biodegradable, and allow formulation with proteins/cytokines without significantly affecting the protein activity upon release. The polymers useful for preparing these layers include any number of biodegradable polymer systems (pure or mixtures) known in the field. The repair mediators that are loaded into the layers can be selected to promote epithelial migration and proliferation, increasing the rate of reepithelialization to effect more rapid and complete wound repair. Each biodegradable polymer layer can be readily formulated to contain one or more repair mediators for delivery. The multilayer architecture, as well as the characteristics of the polymers used in each layer, is chosen such that delivery of repair mediators occurs in a choreographed manner.

The rate of repair mediator release, as well as the duration and sequence of release can be controlled by the adjustment of parameters such as layer thickness, polymer density, repair-mediator loading etc. For instance, increasing the chain length of the primary polymer in a formulation will result in a layer with increased density, which will generally give a slower rate of hydrolysis and a correspondingly reduced rate of repair mediator release. Furthermore, layer thickness can be varied.

Taking the example of a protein as repair mediator, for a given polymer composition and protein concentration, also known as "protein loading", a thicker layer will release protein over a longer time period than a thinner layer. Moreover, the protein loading can be varied to achieve a desired rate of release.

An RLRF which does not have any mixing between layers and contains only one repair mediator in each layer is likely to release only one type of repair mediator at a time. This strategy may be suitable for applications requiring sequential release of single proteins. However, layers can be doped with multiple repair mediators in desired concentrations. If desired, a protein gradient can be prepared by, for example, allowing mixing to take place between the upper portion of one layer which has not completely solidified and the lower portion of the overlying layer as it is being formed into a film. Additionally, if it is critical that the release of one mediator cease before the delivery of another, a relatively thin, non-doped layer can be interposed between two layers to serve as a buffer.

The polymers used in the preparation of the repair mediator-doped layers are biodegradable polymers which undergo a biodegradation. The present invention has a general applicability, and the RLRF can be prepared which functions by undergoing any of a number of types of degradation, including chemical, enzymatic and hydrolytic-type degradations. In one embodiment, for would healing applications, polymers are selected which can be degraded by hydrolysis.

Polymers such as the types mentioned for the barrier layer can be used. Additionally, if unimpeded degradation of mediator-doped layers is desired, polymers in which water-repellent groups do not segregate at the layer surface may be used.

Suitable examples of repair mediator doped layers include the following: polyester-b-PDMS-b-polyester triblock copolymers; PLA; PGA; PGA+PLLA; PLGA; PLA-Fluorocarbon; PLA-PDMS-PLA; PLA-PEO-PLA; block copolymers of PEO and PLA; polysebacic anhydride (PSA); polyfumaric anhydride (PFA); and polyamino acids.

Figure 1C:
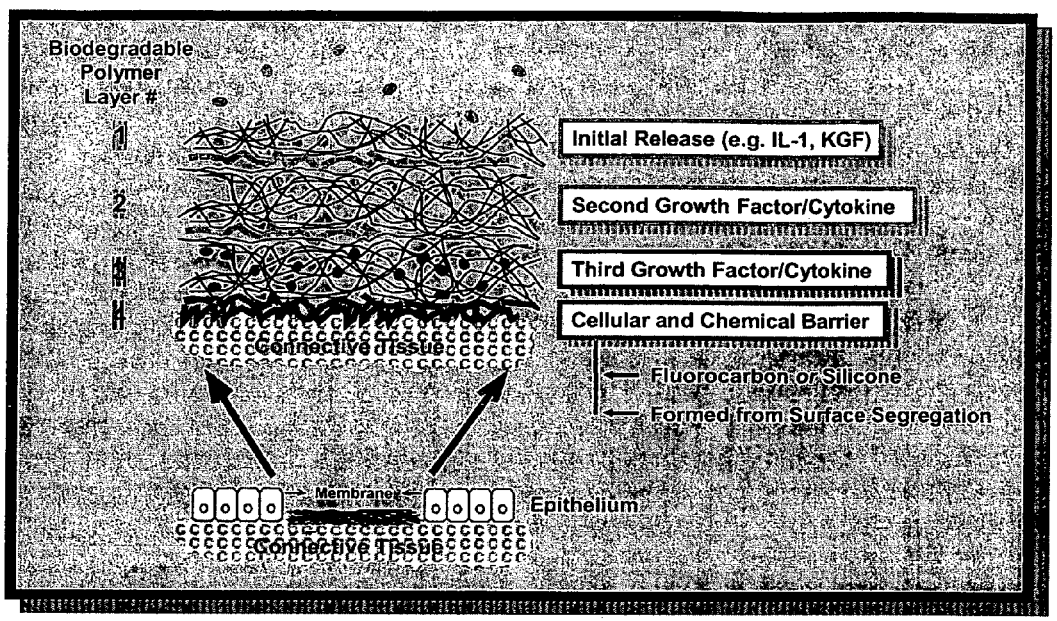
FIG. 1C is a schematic representation of the application of RLRF to a would site and the degradation of RLRF layers.
Figure 6:
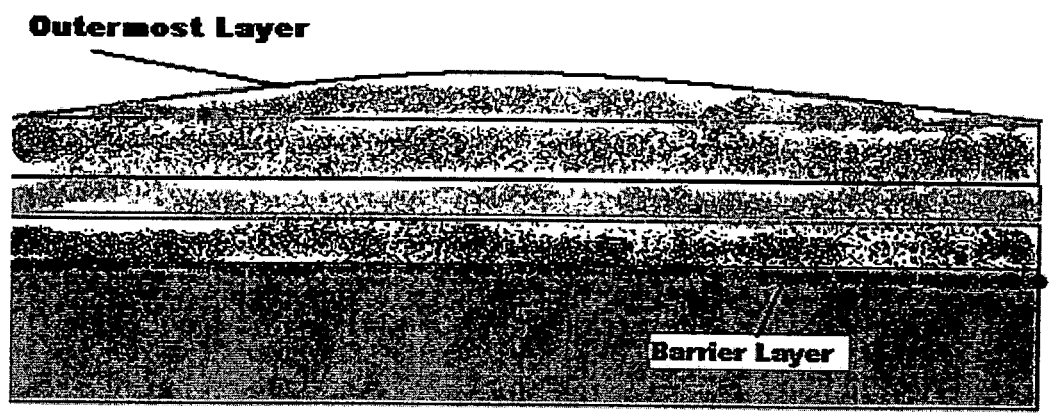
FIG. 6: A representation of one embodiment of the RLRF, wherein one or more layers of the RLRF are convex shaped (thicker in the middle).

For use in wound healing, the RLRF of an appropriate dimension in placed on the wound surface with its barrier layer facing the connective tissue component of the injured site. It is considered that the barrier layer will inhibit the migration of inhibitory factors to the lumenal surface of the RLRF while the degradation of the repair mediator doped layers will release the repair mediators thereby facilitating reepithelialization. An illustration of the process is shown in FIG. 1C. In some environments, degradation of upper layers may proceed at such a rate that central areas of an RLRF may substantially degrade before they are reached by the growth of epithelial cells. If the newly formed cells have need of the repair mediators in the upper layers, the effect of premature degradation can be countered by preparing an RLRF in which some or all of the layers are thicker in the middle than they are at their edges. (See FIG. 6)

If the repair mediator is a protein, it is preferred that the repair mediator-doped layers, one atop the other, keep the sequestered proteins in an active form.

The barrier layer and repair mediator-doped layers can be prepared by methods known in the art which can be used to form thin layers such as pouring methods. One method, carried out under ambient conditions, is as follows: Separate solutions of each biodegradable polymer in a suitable solvent (e.g., $CH_3Cl$) are prepared. In a non-limiting example, a typical polymer concentration is 3% by weight. If additives are to be used, separate solutions of each additive (for example, Aerosol-OT, AOT) in a suitable solvent (e.g., $CH_3Cl$) are prepared. The molar ratio of water or buffer to additive can be adjusted as desired. Separate solutions of each repair mediator are prepared in a suitable aqueous buffer (not necessary for preparation of barrier layer). The desired polymer solutions in the desired ratio are mixed and the desired quantity of additive is added. The desired quantity of repair mediator is added to create a final mixture (not necessary for preparation of barrier layer). The final mixture is gently agitated.

To prepare a film, an aliquot (100-400 µL) of the final mixture is deposited onto a 2 cm×2 cm glass microscope slide. The slide is spun for a short time (1-30 s) between 100 and 3000 rpm to create the repair mediator loaded biodegradable polymer formulation/film. The glass slide us used simply as a support for testing. The exact film thickness depends on the substrate chemistry, the casting solvent, the concentration of all the components in the casting solution. An RLRF is formed by repeating this process, forming additional layers upon the initial layer.

The optimal formulation of components (polymers, additives, pH buffer, etc.), may be different for each repair mediator.

The RLRF (barrier plus repair mediator layers) preferably has a total thickness of up to 1000 microns. Each layer can be as thin as 0.1 microns. In one embodiment, the thickness is less than 500 microns. Flexibility can decrease with thickness. However, if a particular application does not require a high degree of flexibility, thicknesses greater than 1000 microns can be used. Similarly, the lower limit of thickness is limited by repair mediator molecular size. Thus, films of less than 0.1 microns can be used if the size of the repair mediator does not interfere with the ability of the polymer to form a film.

Once the RLRF is prepared, optionally, quantitative time-of-flight secondary ion mass spectrometry (ToF-SIMS) can be used to determine the molecular weight distributions (MWD) of the oligomeric hydrolysis reaction products at the surface of biodegradable polymers as well as drug (protein) release described in U.S. Pat. No. 6,670,190, incorporated herein by reference. The release from drug-loaded, biodegradable polymer blend matrices is governed by both drug diffusion and polymer degradation. Water penetration into the polymer layers is a key factor in determining the overall rate of polymer degradation and the rate of drug release. For hydrophobic drugs, release can be initially controlled by diffusion through any existing pores in the polymer structure, and later by polymer degradation. A co-pending patent application owned by the same assignee describes the determination polymer degradation U.S. patent application No. 20040203161, incorporated herein by reference.

In addition to the above example, the layers of the RLRF can be prepared by various methods known to those skilled in the art including but not limited to spin casting, solution casting, extrusion, printing, rolltrusion, blow molding and aerosol. The device can be made into any shape. The thickness of the device can be varied depending upon the thickness of each individual layer and the number of layers placed on top of the barrier layer. RLRF can be inserted into an injured area by any standard method known to those skilled in the art and secured, if necessary. Such methods include simple placement, adhering to the wound site by using various types of biodegradable glues (such as fibrin glues) and suturing.

The RLRF can be tailored to the particular use. Thus, the time of release of the repair mediators from the repair mediator-doped layers can be varied or the repair mediators themselves can be selected based upon the site where the RLRF is to be used. For example, in the large conducting airway, KGF, IL-1, and TGF-α appear to be important players in epithelial repair. IL-4, IL-13, interferon (IFN)-γ, play leading roles in barrier function and wound healing in Calu-3 human lung epithelial cells. Similarly, EGF, TGF-α, hepatocyte growth factor (HGF), and trefoil factors (TFFs) are involved in gastric mucosa epithelial reconstitution. The biodegradable polymer layers may be prepared that have other reepithelialization/wound healing agents in addition to or instead of these proteins.

Some non-limiting examples where RLRF can be used are blood vessels, the gastrointestinal tract, cornea, skin, respiratory system and liver. There presently exist multiple potential clinical applications of the RLRF in ophthalmologic surgery. A partial listing includes ocular reconstruction for tumor excision, conjunctiva transplantation, pterygium surgery, treatment of persistent corneal ulcerations, treatment of bullous keratopathy and the treatment of cicatrizing diseases of the conjunctivae such as ocular pemphigoid and Stevens Johnson syndrome.

Additionally the RLRF could serve as a carrier for stem cell transplantation for ocular surface replacement. Presently the substance used for some of the above procedures is amniontic membrane that carries with its use the potential for disease transmission such as Hepatitis and HIV.

The following examples are provided to further illustrate this invention.

EXAMPLE 1

This example illustrates the discrimination of active versus inactive protein to optimize use in RLRF layers. In this example, KGF was labeled with fluorescein isothiocyanate (FITC) and purified. A standard steady-state fluorescence anisotropy immunoassay was conducted by using mouse anti-human KGF as the active KGF-selective ligand. Standard titrations on a set of KGF samples were performed to assess our ability to discriminate and quantify active and inactive KGF. The samples were:
1. A fixed amount of native KGF dissolved in pH 7.5 phosphate buffered saline that has not been subjected to any denaturant. This represents active KGF.
2. A fixed amount of KGF that had been subjected to 1 M GdHCl and had removed all the GdHCl from the sample, assuring no denaturation of the anti-human KGF antibody. This represents slightly denatured KGF.
3. A fixed amount of KGF that had been subjected to 4 M GdHCl, with all the GdHCl removed to assure no denaturation of the ligand, is mixed with an equal molar amount of native KGF. This represents a mixture of active and inactive KGF.

Figure 2:
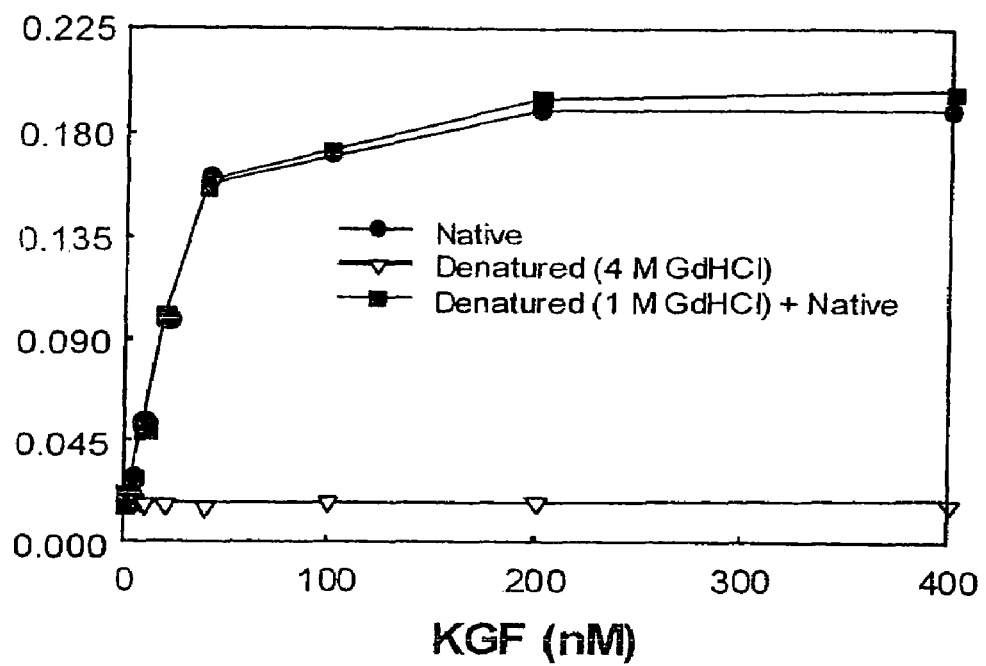
FIG. 2: Homogeneous fluorescence polarization immunoassay to discriminate native, inactive, and a mixture of native and inactive keratinocyte growth factor (KGF).

The results of these experiments are summarized in FIG. 2. KGF denatured only slightly by 1 M GdHCl is not recognized by the anti-KGF antibodies. In contrast, the anti-human KGF antibodies readily recognize the native KGF or selectively bind only to the native KGF proteins in a binary mixture that contains active and inactive/denatured KGF. Together, these results show that a simple assay allows rapid discrimination, in a rigorous fashion, between active and inactive forms of KGF in the supernatant surrounding the RLRF. By using this or other similar assays, formulations providing active forms of repair mediators can be identified.

EXAMPLE 2

This example describes the delivery of active protein from a biodegradable polymer formulation.

Table 1 compiles kinetic and activity results for the release of KGF from four different biodegradable polymer film formulations. These particular films were 6.0±0.2 μm thick and contained 25 ppm KGF.

TABLE 1

Results for KGF in four film formulations (n (no. of replicates) = 5). Release experiments performed in isotonic saline at 35° C.

| Film Type | Average Release Rate (ng/hr) | % Total KGF Released in 10 hrs | % of Released KGF that is Active |
|---|---|---|---|
| PLLA | 24 ± 3 | 1.9 ± 0.1 | 4 ± 4 |
| PLLA + AOT[a] | 39 ± 6 | 2.1 ± 0.2 | 9 ± 4 |
| PLLA/PGA[b] | 83 ± 11 | 19 ± 2 | 12 ± 3 |
| PLLA/PGA/AOT[c] | 94 ± 16 | 27 ± 4 | 58 ± 5 |

[a]Average MW = 55 kDa; 0.09 M AOT; molar ratio of water to AOT = 15, solvent = cyclohexanol.
[b]45% PLLA (55 kDa); 55% PGA (22 kDa); solvent = chloroform.
[c]80% PLLA (40 kDa); 20% PGA (22 kDa); 0.15 M AOT; molar ratio of water (pH 7.8, 0.01 M) to surfactant of 11; solvent = chloroform.

The data in Table 1 show that KGF released from a PLLA film is inactive based on the KGF binding assay. The KGF activity can be improved slightly by using AOT with PLLA (from 4% to 9%). However, blended formulations having combination of PGA and PLLA yielded a biodegradable formulation that is superior to any PLLA/AOT formulation investigated (12% vs. 9% activity upon release). Finally, when we combined PLLA, PGA, and AOT we discovered a formulation that releases 27% of the KGF loaded into the thin film within 10 hrs and 58% of that KGF released from the film is, by the anti-KGF binding assay, active.

Figure 3:
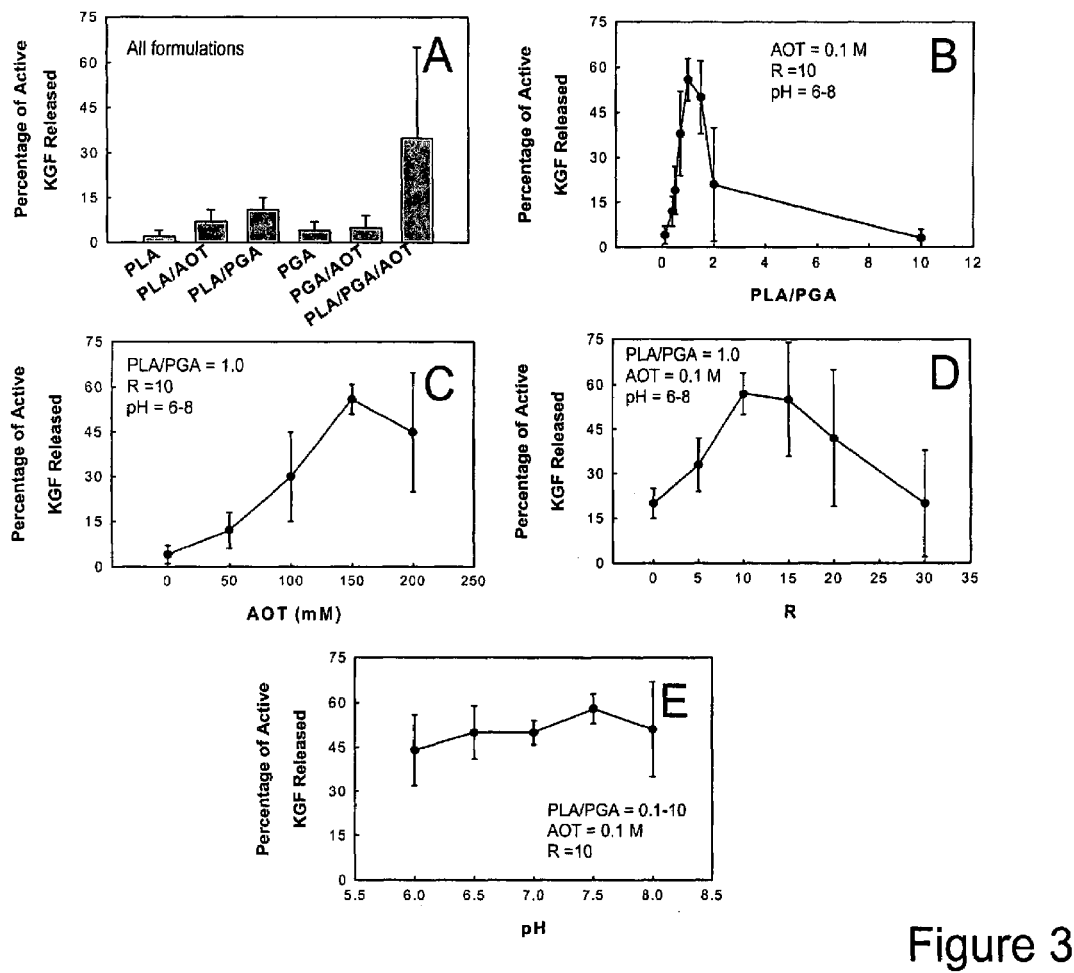
FIG. 3: Effects of composition (Panel A), PLA/PGA weight ratio (Panel B), AOT concentration (Panel C), molar ratio of water to AOT, R (Panel D), and water pH (Panel E) on the percentage of active KGF released from a given formulation. 125 formulations were selected at random amongst the 2,500 that were printed and screened. The pure PLLD formulations behave much like the pure PLA formulations.

In FIG. 3 we summarize the effects of composition, PLA/PGA weight ratio, AOT concentration, molar ratio of water-to-AOT (R), and water pH on the percentage of active KGF released from 125 randomly selected formulations. These results demonstrate several key points. First, the combination of PLA, PGA, and AOT are required to yield liberated KGF that is active per our immunoassay; no binary combination produced as high a fraction of active KGF as the ternary formulation. Second, the more attractive formulations, yielding the highest fraction of active KGF, had the following general features: PLA/PGA (w/w) near unity, AOT loading between 100-200 mM, AOT/water mole ratio of 10-20, and aqueous solution pH between 6 and 8. Again, PLA or PDLL alone cast from chloroform delivered KGF, but that KGF did not bind to either anti-KGF antibody.

EXAMPLE 3

This embodiment describes choreographed Release of KGF and IL-1 from a Partial RLRF. We have choreographed the release of two different proteins from within a RLRF-like architecture by preparing a two-layer laminate structure spin casting a 3.7±0.1 μm thick PLLA film (60 kDa) onto a fused silica cover slip. We then spun cast, on top of the first layer, a second PLLA (60 kDa) film that is 0.4±0.1 μm thick. The thicker layer contained 25 ppm IL-1 that we had labeled with the fluorescent probe BODIPY 650/665. This species excites and emits at 650 and 665 nm, respectively. The thinner layer contained 25 ppm KGF that we had labeled with the fluorescent probe BODIPY 630/650. This species excites and emits at 630 and 650 nm, respectively. The protein-doped, two-layer laminated film was immersed in a cuvette containing isotonic saline. Our flourimeter was configured to sequentially excite the solution surrounding the film at 630 nm while monitoring emission at 650 nm and then rapidly switching (<2 s) to excite at 650 nm while monitoring emission at 665 nm. The film itself was not illuminated during these experiments; only fluorescence from within the buffer, arising from liberated/released proteins from the films was measured. In this way we can simultaneously quantify the release of IL-1 and KGF from the two-layer architecture. The results (FIG. 4) demonstrate that KGF is released from the two-layer structure in a manner indicating that it is in the top layer. There was no detectable IL-1 released during the KGF release event. IL-1 is only released after the KGF-loaded top film layer has eroded away. At this point, the IL-1 begins to be released as the thicker film starts to erode. The differences in kinetic profiles, save the time lag, arise from differences in film thickness and differences in the total number of moles of protein within each film layer. Together these results demonstrate choreographed protein release.

EXAMPLE 4

Figure 4:
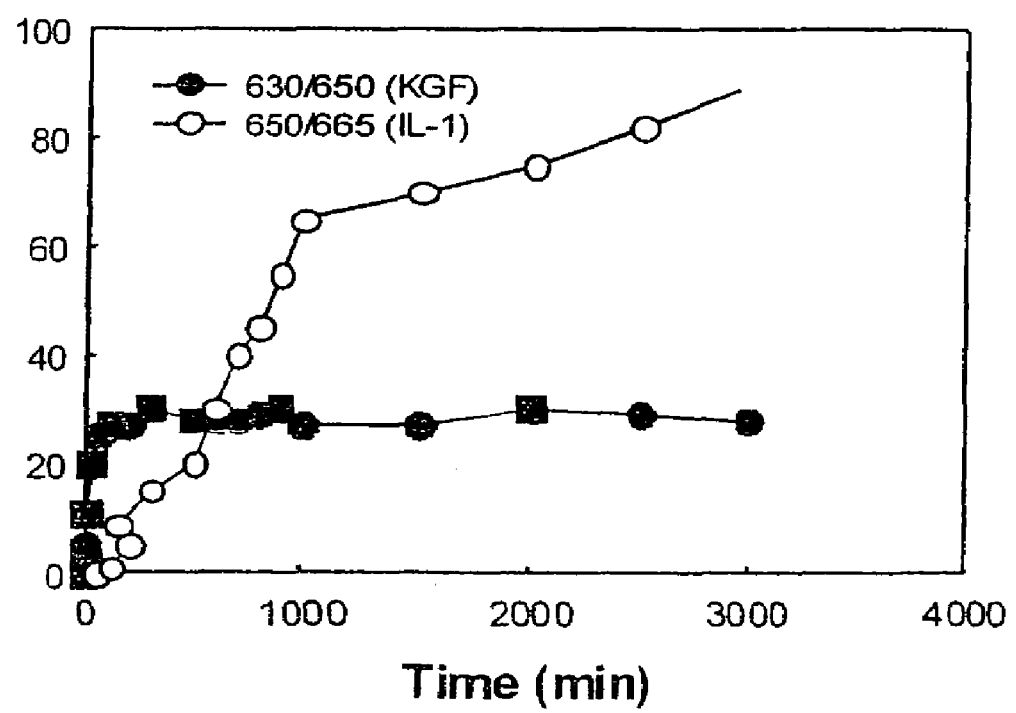
FIG. 4: The choreographed release of two proteins from a two-layer RLRF-like architecture. Top layer (0.4 µm thick) contained KGF. Bottom layer (3.7 µm thick) contained interleukin (IL)-1. The release of KGF occurs first and exclusively as the top layer erodes. The release of IL-1 follows only after the KGF release is complete and the IL-1 release then occurs exclusively.
Figure 5:
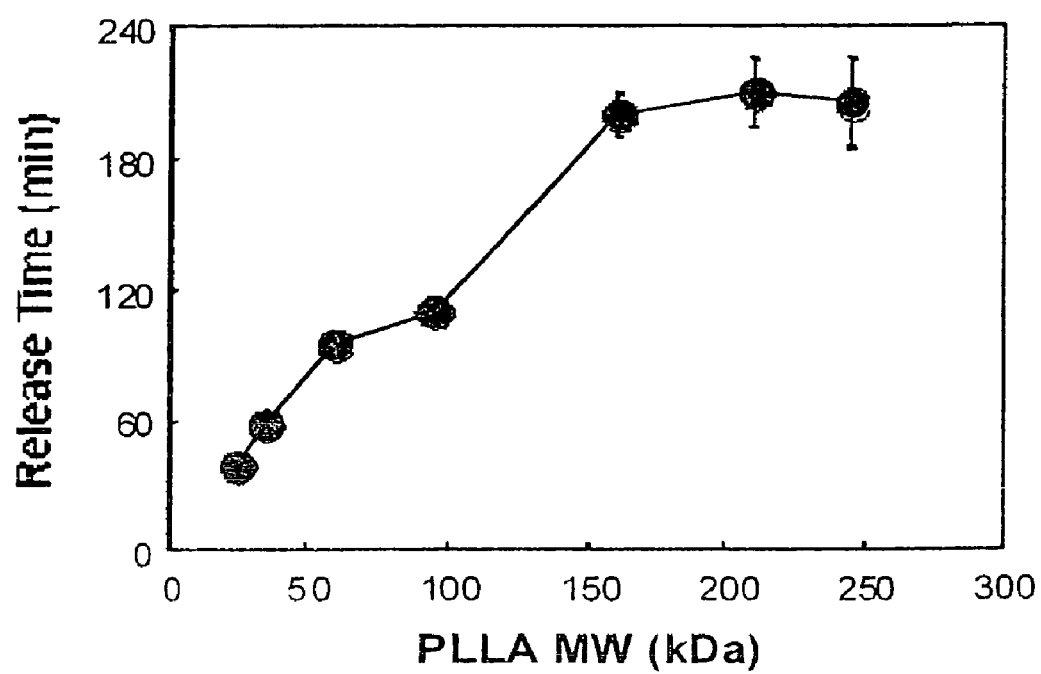
FIG. 5: Controlling the release kinetics from a biodegradable film. Effects of poly(L-lactic acid) (PLLA) molecular weight on the average release time (defined as the time required to reach 90% of the total protein released). The film thickness is the same for all experiments (0.4 µm).

This embodiment describes controlling protein release kinetics. We also investigated additional ways to tune the protein release kinetics from RLRF. (The results in Table 1 show that we can tune the release kinetics by using different components within the formulations and FIG. 4 illustrates that one can adjust the amount of protein delivered and the delivery window by simply adjusting the film thickness.) The results in FIG. 5 show that we can also tune the KGF release kinetics from a film of constant thickness (0.4±0.1 μm) by simply adjusting the average molecular weight of the biodegradable polymer.

We claim:

1. A multilayer film comprising:
   a) a barrier layer comprising polymeric materials, wherein the barrier layer has a lumenal surface and an external surface; and
   b) one or more repair mediator-doped layers which are layered on the lumenal surface of the barrier layer such that the uppermost layer has an exposed surface, each repair mediator-doped layers comprising polymeric material and at least one repair mediator;
   wherein each of said layers is biodegradable, wherein the uppermost layer degrades faster than the barrier layer, and wherein repair mediators are released upon degradation of the one or more repair mediator doped layers.

2. The multilayer film as in claim 1, wherein the barrier layer comprises a siloxane-containing polymer, and wherein the lumenal surface of the barrier layer, the external surface of the barrier layer or both comprise segregated siloxane groups.

3. The multilayer film as in claim 1, wherein the barrier layer comprises a fluorocarbon-containing-containing polymer, and wherein the lumenal surface of the barrier layer, the external surface of the barrier layer or both comprise segregated fluorocarbon groups.

4. The multilayer film as in claim 1 wherein interchain mixing of the barrier layer polymer and the polymer of the adjacent repair mediator doped layer occurs at the interface of said layers.

5. The multilayer film as in claim 1 comprising at least two repair mediator doped layers which share an interface, wherein said interface comprises repair mediators from both of the repair mediator doped layers.

6. A multilayer film as in claim 1, wherein the barrier layer comprises one or more polymers selected from the group consisting of polyester-b-PDMS-b-polyester triblock copolymers, F-polyester, PLA, PGA, PGA+PLLA, PLGA, PLA-Fluorocarbon, PLA-PDMS-PLA, PLA-PEO-PLA, block copolymers of PEO and PLA, polysebacic anhydride (PSA) and polyfumaric anhydride (PFA), polyamino acids, and a polymer comprising siloxane in an ABA poly(dimethylsiloxane) (PDMS) polyester block copolymer.

7. A multilayer film as in claim 1 wherein one or more of the repair mediator-doped layers comprise one or more of the polymers selected from the group consisting of: polyester-b-PDMS-b-polyester triblock copolymers; PLA; PGA; PGA+PLLA; PLGA; PLA-Fluorocarbon; PLA-PDMS-PLA; PLA-PEO-PLA; block copolymers of PEO and PLA; polysebacic anhydride (PSA); polyfumaric anhydride (PFA); and polyamino acids.

8. A multilayer film as in claim 4, wherein the barrier layer and the repair mediator doped layer adjacent to the barrier layer comprises poly-lactic acid (PLA).

9. The multilayer film as in claim 1 wherein at least one of the repair mediator doped layers comprise a PLLA/PGA/AOT mixture.

10. The multilayer film of claim 1, wherein the multilayer film comprises at least two repair mediator doped layers and at least two of the repair mediator doped layers have different thicknesses or different polymer compositions.

11. A method for choreographed release of repair mediators from a multilayer film comprising:
   a) providing a multilayered film comprised of:
      A) a barrier layer comprising polymeric materials; wherein the barrier layer has a lumenal surface and an external surface, and B) one or more repair mediator-doped layers which are layered on the lumenal surface of the barrier layer, with the uppermost layer having an exposed surface, the one or more repair mediator-doped layers comprising polymeric material and at least two repair mediators wherein the uppermost layer degrades faster than the barrier layer, b) exposing the multilayer film to degradation conditions, wherein the repair mediators are released upon degradation of the multilayered film.

12. The method as in claim 11, wherein the barrier layer comprises a siloxane-containing polymer, and wherein the lumenal surface, the external surface of the barrier layer or both comprise segregated siloxane groups or segregated fluorocarbon groups.

13. The method as in claim 11 wherein interchain mixing of the barrier layer polymer and the polymer of the adjacent repair mediator doped layer occurs at the interface of said layers.

14. The method of claim 11, wherein the barrier layer comprises one or more polymers selected from the group consisting of polyester-b-PDMS-b-polyester triblock copolymers, F-polyester, PLA, PGA, PGA+PLLA, PLGA, PLA-Fluorocarbon, PLA-PDMS-PLA, PLA-PEO-PLA, block copolymers of PEO and PLA, polysebacic anhydride (PSA) and polyfumaric anhydride (PFA), polyamino acids, and a polymer comprising siloxane in an ABA poly(dimethylsiloxane) (PDMS) polyester block copolymer.

15. The method of claim 11, wherein one or more of the repair mediator-doped layers comprise one or more of the polymers selected from the group consisting of: polyester-b-PDMS-b-polyester triblock copolymers; PLA; PGA; PGA+PLLA; PLGA; PLA-Fluorocarbon; PLA-PDMS-PLA; PLA-PEO-PLA; block copolymers of PEO and PLA; polysebacic anhydride (PSA); polyfumaric anhydride (PFA); and polyamino acids.

16. The method of claim 13, wherein the barrier layer and the repair mediator doped layer adjacent to the barrier layer comprises poly-lactic acid (PLA).

17. The method of in claim 11 wherein at least one of the repair mediator doped layers comprise a PLLA/PGA/AOT mixture.

18. The multilayer film of claim 11, wherein the repair mediators are selected from the group consisting of IL-1, IL-3, IL-4, KGF, TGF-α, IL-13, IFN-γ, EGF, HGF and TFFs.

19. A method for promoting the healing of a surface wound, said method comprising the steps of applying, to at least a portion of said surface, a multilayer film comprising:

a) a barrier layer comprising polymeric materials, wherein the barrier layer has a lumenal surface and an external surface; and b) one or more repair mediator-doped layers which are layered on the lumenal surface of the barrier layer such that the uppermost layer has an exposed surface, each repair mediator-doped layers comprising polymeric material and at least one repair mediator;

wherein each of said layers is biodegradable, wherein the uppermost layer degrades faster than the barrier layer, and wherein repair mediators are released upon degradation of the one or more repair mediator doped layers.

20. The method as in claim 19, wherein the barrier layer comprises a siloxane-containing or fluorocarbon-containing polymer, and wherein the lumenal surface, the external surface of the barrier layer or both comprise segregated siloxane groups or segregated fluorocarbon groups.

21. The method of claim 19, wherein the barrier layer comprises one or more polymers selected from the group consisting of polyester-b-PDMS-b-polyester triblock copolymers, F-polyester, PLA, PGA, PGA+PLLA, PLGA, PLA-Fluorocarbon, PLA-PDMS-PLA, PLA-PEO-PLA, block copolymers of PEO and PLA, polysebacic anhydride (PSA) and polyfumaric anhydride (PFA), polyamino acids, and a polymer comprising siloxane in an ABA poly(dimethylsiloxane) (PDMS) polyester block copolymer.

22. The method of claim 19, wherein one or more of the repair mediator-doped layers comprise one or more of the polymers selected from the group consisting of: polyester-b-PDMS-b-polyester triblock copolymers; PLA; PGA; PGA+PLLA; PLGA; PLA-Fluorocarbon; PLA-PDMS-PLA; PLA-PEO-PLA; block copolymers of PEO and PLA; polysebacic anhydride (PSA); polyfumaric anhydride (PFA); and polyamino acids.

23. The method of claim 19, wherein the barrier layer and the repair mediator doped layer adjacent to the barrier layer comprises poly-lactic acid (PLA).

24. The method of in claim 19 wherein at least one of the repair mediator doped layers comprise a PLLA/PGA/AOT mixture.

25. The multilayer film of claim 11, wherein the repair mediators are selected from the group consisting of IL-1, IL-3, IL-4, KGF, TGF-α, IL-13, IFN-γ, EGF, HGF and TFFs.

* * * * *